United States Patent [19]
Herrin

[11] Patent Number: 6,148,820
[45] Date of Patent: Nov. 21, 2000

[54] APPARATUS FOR INHIBITING NOCTURNAL DRYING OF THE ORAL CAVITY

[75] Inventor: Hermon K. Herrin, Bellaire, Tex.

[73] Assignee: The Board of Regents of the University of Texas System, Austin, Tex.

[21] Appl. No.: 09/347,762

[22] Filed: Jul. 6, 1999

[51] Int. Cl.[7] ..................................... A61F 11/00

[52] U.S. Cl. ............... 128/857; 2/206; 2/9; 128/859; 128/848

[58] Field of Search ............... 2/206, 9; 602/61; 128/857, 850, 848, 859, 863

[56] References Cited

U.S. PATENT DOCUMENTS

| | | | |
|---|---|---|---|
| 1,216,679 | 2/1917 | Foster | 128/848 |
| 1,296,946 | 3/1919 | Galiardo | 128/848 |
| 5,706,802 | 1/1998 | McCormick. | |
| 5,785,052 | 7/1998 | Johnson. | |

*Primary Examiner*—Michael A. Brown
*Assistant Examiner*—Lalita M. Hamilton
*Attorney, Agent, or Firm*—Duane, Morris & Heckscher LLP

[57] ABSTRACT

The present invention relates to an apparatus for inhibiting nocturnal drying of the oral cavity from breathing through a person's mouth. More particularly, the invention is directed to an apparatus comprising an air permeable cover, an elastic strap attached to the cover for securing the cover to a person's face, and a cup attached to the lower region of the cover for securing a person's chin.

15 Claims, 2 Drawing Sheets

APPARATUS FOR INHIBITING NOCTURNAL DRYING OF THE ORAL CAVITY

BACKGROUND OF THE INVENTION

1. Field of the Invention

The present invention relates to an apparatus for inhibiting nocturnal drying of the oral cavity from breathing through a person's mouth. More particularly, the invention is directed to an apparatus comprising an air permeable cover, an elastic strap attached to the cover for securing the cover to a person's face, and a cup attached to the lower region of the cover for securing a person's chin.

2. Description of the Prior Art

Xerostomia is the term used for a dry mouth. Millions of Americans suffer from this problem to one degree or another. The problem is most severe at night when an individual may be awakened numerous times at night with discomfort resulting from the dryness in their oral cavity as a result of breathing through their mouth complicated by a host of factors that predispose them to problems of xerostomia.

The etiology of xerostomia is multi-factorial. Many drugs are known to inhibit or reduce salivary function. Among these drugs are many commonly prescribed medications such as tricyclic antidepressants, beta-blockers, and opioid pain medications. Xerostomia can also be the result of diseases such as Sjogren's or other auto immune diseases. Patients who are treated for neoplasms in the head and neck with radiation will suffer a permanent loss of salivary function of any salivary gland included in the treatment field.

The pain of patients who suffer mucositis during cancer treatment can be minimized to some degree by the prevention of mouth breathing which acts to dry out the already inflamed oral tissues making these tissues more susceptible to infection and painful inflammation.

Prior art methods for dealing with xerostomia include waking up during the night and drinking water or some other beverage to moisten the oral cavity. This prior art method is disruptive to a person's sleep pattern and often results in reduced efficiency for the person during the day due to inadequate sleep at night.

The present invention provides an improved means for inhibiting nocturnal drying of the oral cavity. The present invention reduces a person's respiration through the oral cavity while increasing a person's respiration through the nasal cavity, effectively redistributing a person's respiratory flow. This redistribution permits a person to sleep for longer periods without the need to wake up and ingest a beverage.

SUMMARY OF THE INVENTION

The present invention is directed toward an apparatus for inhibiting nocturnal drying of the oral cavity from breathing through a person's mouth. The present invention comprises an air permeable cover having a sufficient surface area to cover a person's mouth without covering a person's nose. The cover comprises a first side region, a second side region, and a lower region.

The invention further comprises an elastic strap having a first end attached to the first side region of the cover and a second end attached to the second side region of the cover. The strap has a sufficient length to extend around a person's head when the cover is placed over the person's mouth.

The invention further comprises a cup attached to the lower region of the cover and positioned such that it can engage a person's chin when the cover is placed over the person's mouth and the strap is placed around the person's head.

DESCRIPTION OF THE PREFERRED EMBODIMENTS

Figure 2:
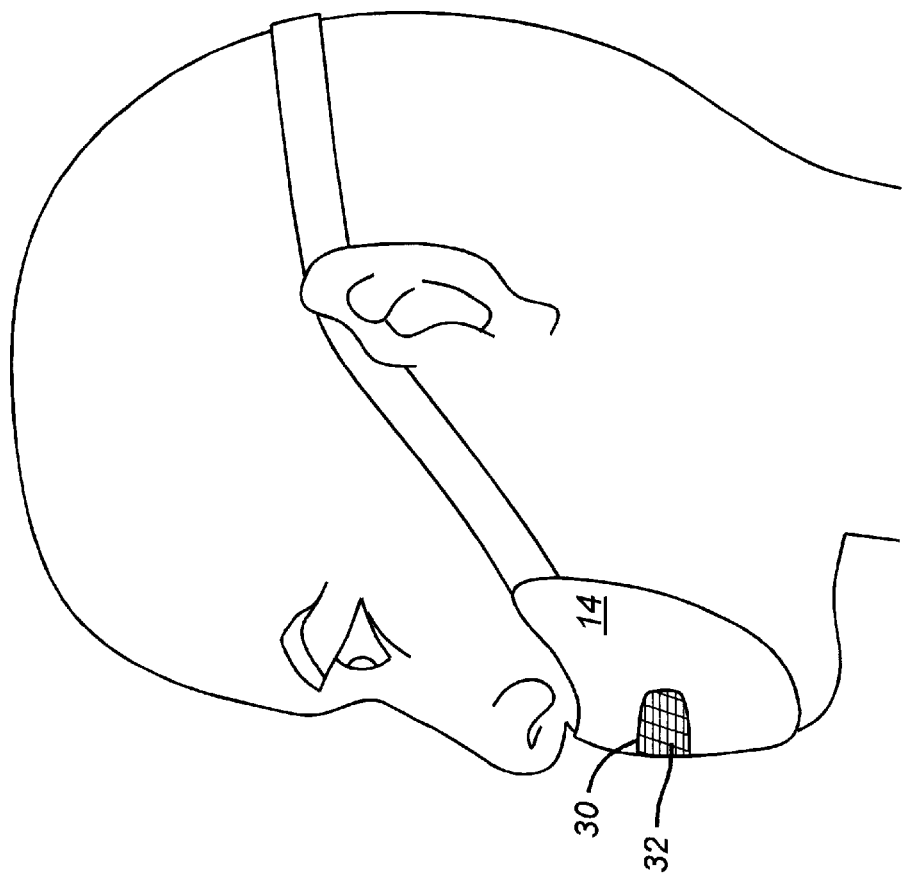
FIG. 2 is a side view of the present invention worn on a user's face.
Figure 1:
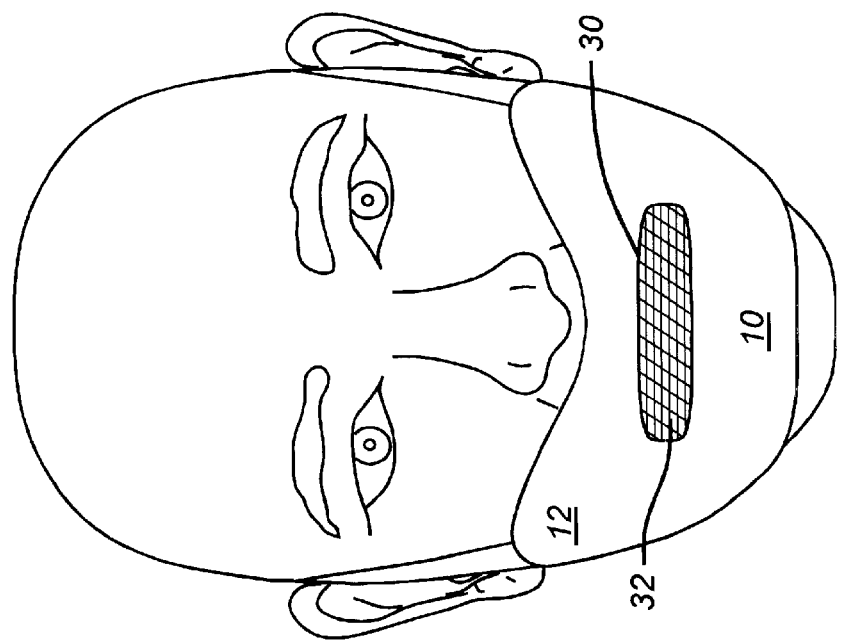
FIG. 1 is a front view of the present invention worn on a user's face.
Figure 3:
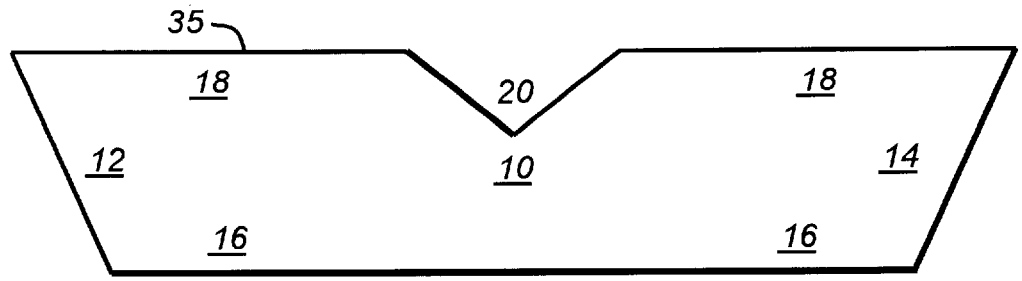
FIG. 3 is a front view of the cover of the present invention.

The present invention comprises an air permeable cover 10 having a sufficient surface area to cover a person's mouth without covering the person's nose, as shown in FIGS. 1–2. The cover has a first side region 12, a second side region 14, and a lower region 16, as shown in FIG. 3. In a preferred embodiment, the cover is made from coffon.

Figure 4:
FIG. 4 is a cross sectional view of a first embodiment of the cover of the present invention.

In a preferred embodiment, the cover comprises two or three layers 17 of cotton cloth, as shown in FIG. 4. In another preferred embodiment, the cover is trapezoidal, as shown in FIG. 3.

Figure 5:
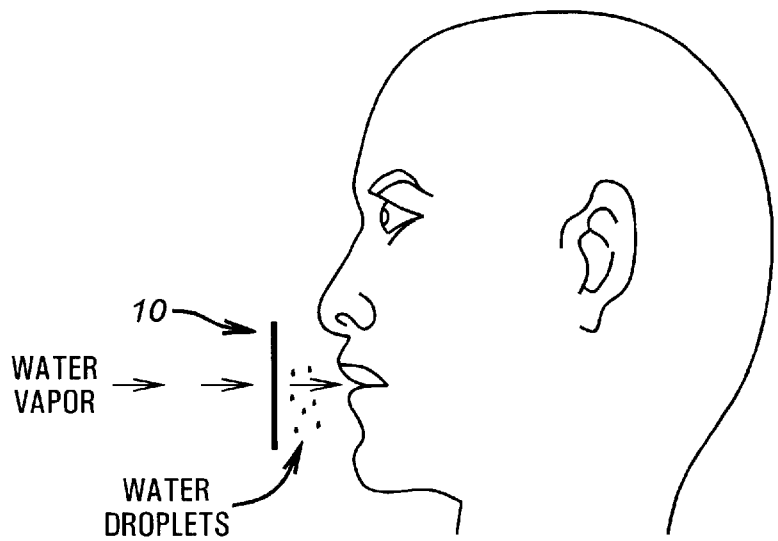
FIG. 5 is a side view of a second embodiment of the cover of the present invention.

In another preferred embodiment, the cover is made from a vapor permeable/liquid impermeable fabric, such as that sold under the trademark GoreTex®. In this embodiment, the GoreTex® fabric cover is positioned over a person's mouth to permit the inhalation of water vapor, while acting as a barrier to the exhalation of liquid droplets by a person. This orientation is accomplished by positioning the vapor permeable side of the cover such that it faces away from the person's mouth and positioning the water impermeable side of the cover such that it faces towards the person's mouth, as shown in FIG. 5. This orientation of the GoreTex® cover is reversed from the conventional orientation of GoreTex® fabric with respect to a person when the fabric is worn as an outer garment.

In another preferred embodiment, the cover comprises an upper region 18 opposite the lower region, as shown in FIG. 3. The upper region comprises an upper edge 35, as shown in FIG. 3. In another preferred embodiment, the upper region of the cover is longer than the lower region. In a preferred embodiment, the upper region comprises a centrally located notch 20, as shown in FIGS. 2 and 3. In a preferred embodiment, the notch extends downward from the upper edge and is V shaped, as shown in FIG. 3.

In a preferred embodiment, the invention further comprises an opening 30 centrally located in the cover and positioned such that when the cover is placed over a person's mouth, the opening is generally aligned with the person's lips, as shown in FIG. 3. In another preferred embodiment, the invention comprises a mesh screen 32, covering the opening, as shown in FIG. 1.

The foregoing disclosure and description of the invention are illustrative and explanatory. Various changes in the size, shape, and materials, as well as in the details of the illustrative embodiments may be made without departing from the spirit of the invention.

What is claimed is:

1. An apparatus for inhibiting nocturnal drying of the oral cavity from breathing through a person's mouth, comprising:

a. a vapor permeable, liquid impermeable cover having a sufficient surface area to cover a person's mouth, without covering a person's nose, said cover having a first side region, a second side region, an upper region, and a lower region;

b. an elastic strap having a first end attached to the first side region of said cover and a second end attached to the second side region of said cover, said strap being of sufficient length to extend around a person's head when the cover is placed over the person's mouth; and c. a cup attached to the lower region of the cover and positioned such that it can engage a person's chin when said cover is placed over the person's mouth and said strap is placed around the person's head.

2. The apparatus of claim 1, wherein said cover is made from cotton.

3. The apparatus of claim 1, wherein said cover is made from a vapor permeable, liquid impermeable fabric positioned to permit the inhalation of water vapor while acting as a barrier to the exhalation of liquid droplets by a person.

4. The apparatus of claim 1, wherein said cover is trapezoidal.

5. The apparatus of claim 4, wherein said upper region comprises an upper edge.

6. The apparatus of claim 5, wherein said upper region is longer than said lower region.

7. The apparatus of claim 5, wherein said upper region comprises a centrally located notch extending downward from said upper edge.

8. An apparatus for inhibiting nocturnal drying of the oral cavity from breathing through a person's mouth, comprising:

a. a cotton cover having a sufficient surface area to cover a person's mouth, without covering a person's nose, said cover having a first side region, a second side region, an upper region comprising an upper edge, and a lower region;

b. a notch centrally located in said upper region and extending downward from said upper edge;

c. an elastic strap having a first end attached to the first side region of said cover and a second end attached to the second side region of said cover, said strap being of sufficient length to extend around a person's head when the cover is placed over the person's mouth; and d. a cup attached to the lower region of the cover and positioned such that it can engage a person's chin when said cover is placed over the person's mouth and said strap is placed around the person's head.

9. The apparatus of claim 8, wherein said cover is trapezoidal.

10. The apparatus of claim 8, wherein said upper region is longer than said lower region.

11. The apparatus of claim 10, wherein said centrally located notch is V shaped.

12. The apparatus of claim 8, wherein said cover is made from a vapor permeable, liquid impermeable fabric positioned to permit the inhalation of water vapor while acting as a barrier to the exhalation of liquid droplets by a person.

13. An apparatus for inhibiting nocturnal drying of the oral cavity from breathing through a person's mouth, comprising:

a. an air permeable cover having a sufficient surface area to cover a person's mouth, without covering a person's nose, said cover having a first side region, a second side region, a lower region, and an upper region opposite from said lower region, said upper region being longer than said lower region and comprising an upper edge;

b. a notch centrally located in said upper region and extending downward from said upper edge;

c. an elastic strap having a first end attached to the first side region of said cover and a second end attached to the second side region of said cover, said strap being of sufficient length to extend around a person's head when the cover is placed over the person's mouth; and d. a cup attached to the lower region of the cover and positioned such that it can engage a person's chin when said cover is placed over the person's mouth and said strap is placed around the person's head.

14. The apparatus of claim 13, wherein said cover is made from a vapor permeable, liquid impermeable fabric positioned to permit the inhalation of water vapor while acting as a barrier to the exhalation of liquid droplets by a person.

15. The apparatus of claim 13, wherein said cover comprises at least two layers of cotton.

\* \* \* \* \*